(12) United States Patent
Yamamoto et al.

(10) Patent No.: US 12,383,772 B2
(45) Date of Patent: Aug. 12, 2025

(54) LIGHT-TRANSMITTING MEMBER AND SHIELD

(71) Applicant: CANON KABUSHIKI KAISHA, Tokyo (JP)

(72) Inventors: Shuhei Yamamoto, Tokyo (JP); Tomonari Nakayama, Tokyo (JP); Yoji Teramoto, Kanagawa (JP); Miwa Takachi, Kanagawa (JP); Shun Ouchi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 817 days.

(21) Appl. No.: 17/494,718

(22) Filed: Oct. 5, 2021

(65) Prior Publication Data

US 2022/0111232 A1 Apr. 14, 2022

(30) Foreign Application Priority Data

Oct. 9, 2020 (JP) .................................. 2020-171319

(51) Int. Cl.
*A62B 18/00* (2006.01)
*A41D 13/11* (2006.01)

(52) U.S. Cl.
CPC ........ *A62B 18/006* (2013.01); *A41D 13/1184* (2013.01)

(58) Field of Classification Search
CPC .......................... A62B 18/006; A41D 13/1184
See application file for complete search history.

(56) References Cited

U.S. PATENT DOCUMENTS

| | | | |
|---|---|---|---|
| 10,420,386 B1* | 9/2019 | Jefferis | .................... A42B 3/20 |
| 2006/0246233 A1 | 11/2006 | Fukuda | |
| 2007/0141114 A1 | 6/2007 | Muisener | |
| 2009/0046379 A1* | 2/2009 | Kuramoto | .............. G02B 5/188 |
| | | | 428/323 |

(Continued)

FOREIGN PATENT DOCUMENTS

| | | |
|---|---|---|
| CN | 105700046 A | 6/2016 |
| JP | 2000280428 A | 10/2000 |

(Continued)

OTHER PUBLICATIONS

[NPL-1] Kawai et al. (JP 2016-001200 A); Jan. 7, 2016 (EPO—machine translation to English). (Year: 2016).*

(Continued)

*Primary Examiner* — Donald M Flores, Jr.
(74) *Attorney, Agent, or Firm* — Canon U.S.A., Inc. IP Division

(57) ABSTRACT

A light-transmitting member includes a substrate including a resin layer, and a functional film disposed on the substrate. The substrate has a thickness of 1 μm or more and less than 1 mm. An optical thickness of the functional film with respect to light having a wavelength of 464 nm or more and 653 nm or less is less than a half of the wavelength. A contact angle of water with respect to an upper surface of the functional film in the light-transmitting member is less than 90°. The functional film has a porous portion containing a plurality of particles. A first particle and a second particle among the plurality of particles are bound to each other with a binder. Each of the first particle, the second particle, and the binder contains an inorganic material.

36 Claims, 8 Drawing Sheets

(56) References Cited

U.S. PATENT DOCUMENTS

| | | | |
|---|---|---|---|
| 2009/0151054 A1* | 6/2009 | Van | A42B 3/286 |
| | | | 2/410 |
| 2010/0035039 A1 | 2/2010 | Jing | |
| 2012/0088106 A1 | 4/2012 | Jing | |
| 2013/0222916 A1 | 8/2013 | Ogane | |
| 2014/0363628 A1* | 12/2014 | Nakai | G01L 5/0033 |
| | | | 428/141 |
| 2015/0011668 A1 | 1/2015 | Kolb | |
| 2015/0017386 A1 | 1/2015 | Kolb | |
| 2015/0323704 A1* | 11/2015 | Nishimura | B32B 27/16 |
| | | | 359/601 |
| 2017/0073524 A1* | 3/2017 | Nakayama | C09D 1/00 |
| 2017/0208878 A1* | 7/2017 | Kakinuma | A61F 9/045 |
| 2019/0187335 A1* | 6/2019 | Nakayama | C23C 14/18 |
| 2020/0049862 A1 | 2/2020 | Ogane | |
| 2020/0186685 A1 | 6/2020 | Watanabe | |
| 2020/0375272 A1 | 12/2020 | Ulmer | |

FOREIGN PATENT DOCUMENTS

| | | | | |
|---|---|---|---|---|
| JP | 2001233611 A | | 8/2001 | |
| JP | 2001328195 A | | 11/2001 | |
| JP | 2002145372 A | * | 5/2002 | |
| JP | 2004142161 A | | 5/2004 | |
| JP | 2004258267 A | | 9/2004 | |
| JP | 2005283611 A | | 10/2005 | |
| JP | 2006330705 A | | 12/2006 | |
| JP | 2007240707 A | | 9/2007 | |
| JP | 2008139581 | | 6/2008 | |
| JP | 2011530401 A | | 12/2011 | |
| JP | 2012108320 A | | 6/2012 | |
| JP | 2013217977 A | | 10/2013 | |
| JP | 2015511254 A | | 4/2015 | |
| JP | 2015161791 A | | 9/2015 | |
| JP | 2016001200 A | * | 1/2016 | C09D 1/00 |
| JP | 2017049313 A | | 3/2017 | |
| JP | 2019211662 A | | 12/2019 | |
| JP | 2020095254 A | | 6/2020 | |
| JP | 2020154014 A | | 9/2020 | |
| JP | 3228026 U | * | 10/2020 | |
| WO | 2006121102 A1 | | 11/2006 | |

OTHER PUBLICATIONS

[NPL-2] Kono (JP 2002-145372 A); May 22, 2002 (EPO—machine translation to English). (Year: 2002).*

[NPL-3] Omasa (JP 3228026 U); Oct. 1, 2020 (EPO—machine translation to English). (Year: 2020).*

* cited by examiner

LIGHT-TRANSMITTING MEMBER AND SHIELD

BACKGROUND

Field of the Disclosure

The present disclosure relates to a light-transmitting member.

Description of the Related Art

Improvement in the functionality of light-transmitting members using resin substrates has been desired. Japanese Patent Laid-Open No. 2005-283611 discloses an antireflection film that includes a light-transmitting base film and a low-refractive-index layer disposed on the base film, in which the low-refractive-index layer contains hollow silica fine particles or porous silica fine particles.

There is a room for improvement in the functionality of the antireflection film disclosed in Japanese Patent Laid-Open No. 2005-283611.

SUMMARY

A first embodiment of the disclosure provides a light-transmitting member including a substrate including a resin layer, and a functional film disposed on the substrate, in which the substrate has a thickness of 1 µm or more and less than 1 mm, an optical thickness of the functional film with respect to light having a wavelength of 464 nm or more and 653 nm or less is less than a half of the wavelength, a contact angle of water with respect to an upper surface of the functional film in the light-transmitting member is less than 90°, the functional film has a porous portion containing a plurality of particles, a first particle and a second particle among the plurality of particles are bound to each other with a binder, and each of the first particle, the second particle, and the binder contains an inorganic material.

A second embodiment of the disclosure provides a light-transmitting member including a substrate including a resin layer, and a functional film disposed on the substrate, in which the substrate has a thickness of 1 µm or more and less than 1 mm, an optical thickness of the functional film with respect to light having a wavelength of 464 nm or more and 653 nm or less is less than a half of the wavelength, a contact angle of water with respect to an upper surface of the functional film in the light-transmitting member is less than 90°, the functional film has a porous portion containing a plurality of particles, a distance between a first particle and a second particle among the plurality of particles is smaller than a size of the first particle, and an empty space is provided between the first particle and the second particle.

A third embodiment of the disclosure provides a light-transmitting member including a substrate including a resin layer, and a functional film disposed on the substrate, in which the substrate has a thickness of 1 µm or more and less than 1 mm, the functional film has a physical thickness smaller than the thickness of the substrate, a contact angle of water with respect to an upper surface of the functional film in the light-transmitting member is less than 90°, the functional film has a porous portion containing a plurality of particles, a distance between a first particle and a second particle among the plurality of particles is smaller than a size of the first particle, an empty space is provided between the first particle and the second particle, and each of the first particle and the second particle is a hollow particle.

A fourth embodiment of the disclosure provides a shield including a light-transmitting member and a holder that holds the light-transmitting member, in which the holder has a structure configured to fix the light-transmitting member to a user such that the light-transmitting member covers at least part of a face of the user, the light-transmitting member includes a substrate including a resin layer, and a functional film disposed on the substrate, the substrate has a thickness of 1 µm or more and less than 1 mm, the functional film has a physical thickness of less than 1 µm, and the functional film contains a plurality of particles.

Further features of the present disclosure will become apparent from the following description of exemplary embodiments with reference to the attached drawings.

DESCRIPTION OF THE EMBODIMENTS

Embodiments implementing the present disclosure will be described below with reference to the drawings. In the following description and drawings, configurations common to a plurality of drawings are assigned the same reference signs. Accordingly, the common configurations may be described with mutual reference to a plurality of drawings without specifying. The description of the configurations assigned the same reference signs may be omitted.

The embodiments provide a technology advantageous to improvement in the functionality of a light-transmitting member.

Figure 1A:
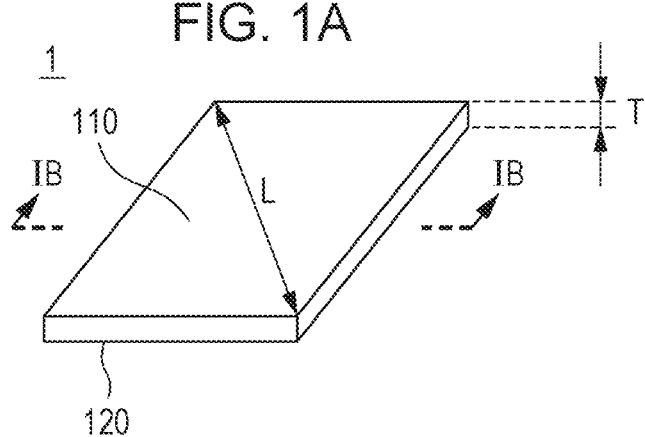
FIGS. 1A to 1C are each a schematic view illustrating an example of a light-transmitting member, according to the subject disclosure.

FIG. 1A is a perspective view of an example of a light-transmitting member 1 according to an embodiment. The light-transmitting member 1 has a film-like, sheet-like, or plate-like shape. When the light-transmitting member 1 has a film-like shape, the light-transmitting member 1 can be referred to as a film. When the light-transmitting member 1 has a sheet-like shape, the light-transmitting member 1 can be referred to as a sheet.

When the light-transmitting member 1 has a plate-like shape, the light-transmitting member 1 can be referred to as a plate. The light-transmitting member 1 has a front surface 110 and a back surface 120, and the front surface 110 and the back surface 120 have substantially the same shape. The distance between the front surface 110 and the back surface 120, that is, a thickness T of the light-transmitting member 1 is much smaller than a maximum width L of the front surface 110 and the back surface 120. For example, the thickness T may be less than 1/1000 of the maximum width L. In this example, the shape of each of the front surface 110 and the back surface 120 of the light-transmitting member 1 is a quadrangle but is not limited thereto.

Figure 1B:
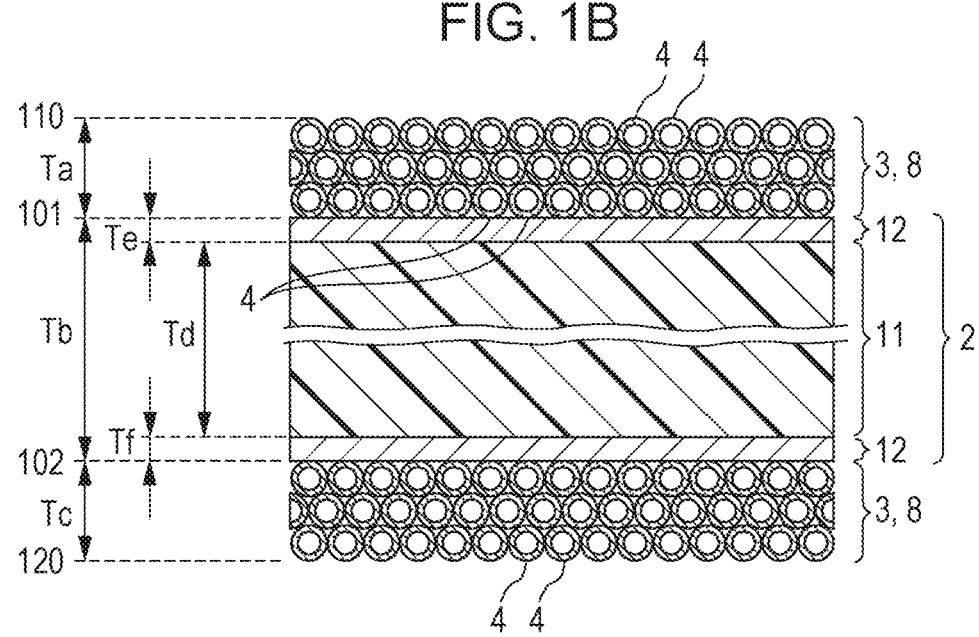

FIG. 1B is a sectional view of the light-transmitting member 1 taken along line IB-IB in FIG. 1A. The light-transmitting member 1 includes a substrate 2 and a functional film 3 disposed on the substrate 2. The substrate 2 can include a resin layer 11. The functional film 3 can include a porous portion 8.

The substrate 2 has two main surfaces 101 and 102 opposed to each other. The distance between the main surface 101 and the main surface 102 is a thickness Tb of the substrate 2. The thickness Tb of the substrate 2 can be 1 μm or more and less than 1 mm. When the thickness Tb of the substrate 2 is less than 250 μm and the light-transmitting member 1 has flexibility, the light-transmitting member 1 can be regarded as a film-like member. When the thickness Tb of the substrate 2 is 250 μm or more and the light-transmitting member 1 has flexibility, the light-transmitting member 1 can be regarded as a sheet-like member. When the light-transmitting member 1 does not have flexibility, the light-transmitting member 1 can be regarded as a plate-like member.

The functional film 3 is disposed on at least one of the main surfaces 101 and 102 of the substrate 2. In this example, the functional film 3 is disposed on each of the two main surfaces 101 and 102 (both surfaces) of the substrate 2. Alternatively, the functional film 3 may be disposed on only one of the two main surfaces 101 and 102 of the substrate 2. When the functional film 3 having the porous portion 8 is disposed on only one surface of the light-transmitting member 1, the surface having the functional film 3 thereon can be the front surface 110, and the other surface having no functional film 3 can be the back surface 120.

The functional film 3 on the main surface 101 has a physical thickness Ta, and the functional film 3 on the main surface 102 has a physical thickness Tc. The physical thicknesses Ta and Tc of the functional films 3 are each smaller than the thickness Tb of the substrate 2 (Ta<Tb, Tc<Tb). Accordingly, the substrate 2 mainly bears the shape and mechanical properties of the light-transmitting member 1. Each of the physical thicknesses Ta and Tc of the functional films 3 may be less than 200 nm. An optical thickness nd of a functional film 3 described later is defined by the product of the refractive index of the functional film 3 and the physical thickness of the functional film 3. The physical thickness Tc may be the same as or different from the physical thickness Ta. For example, the functional film 3 on the front surface 110 side (on the main surface 101) may have a larger thickness than the functional film 3 on the back surface 120 side (on the main surface 102).

Figure 2A:
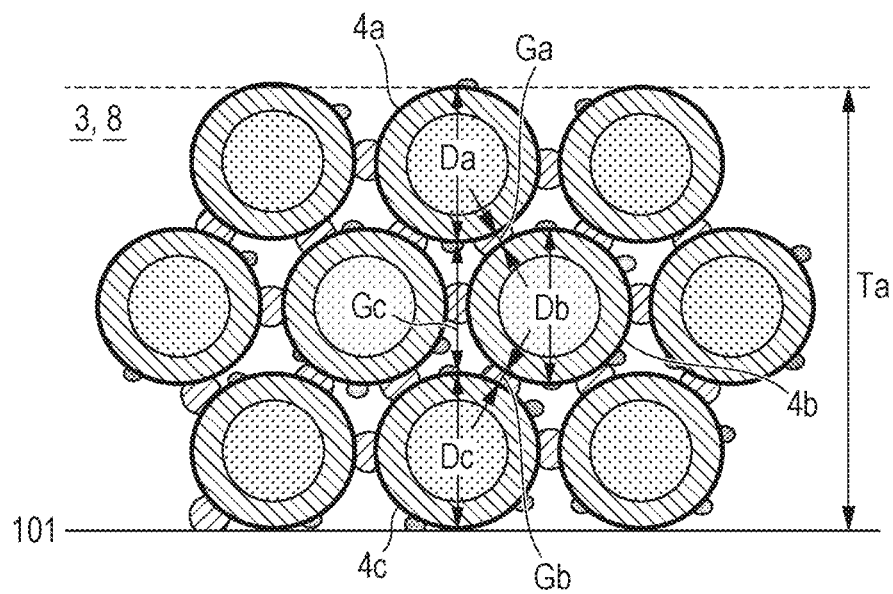
FIGS. 2A and 2B are each a schematic view illustrating an example of a light-transmitting member, according to the subject disclosure.

The functional film 3 can have a porous portion 8. The porous portion 8 contains a plurality (large number) of particles 4. The number of pores in the porous portion 8 correlates with the number of the particles 4. The porous portion 8 has some features. FIG. 2A is an enlarged view of an example of the porous portion 8 and shows a large number of (in this example, ten) particles 4, as illustrated in the legend in FIG. 2A. Among the large number of particles 4, a particle 4a, a particle 4b, and a particle 4c are focused. Although the three particles 4a, 4b, and 4c will be described here, the same applies to the other particles 4. The particles 4 may be arranged such that the particles 4 are stacked so as to form a plurality of layers with respect to the main surface 101 of the substrate 2.

The particle 4a has a size Da, the particle 4b has a size db, and the particle 4c has a size Dc. Here, the sizes Da, db, and Dc are sizes in the film thickness direction of the functional film 3. A distance Ga between the particle 4a and the particle 4b is smaller than the size Da of the particle 4a. The distance Ga between the particle 4a and the particle 4b is smaller than the size db of the particle 4b. An empty space 6 is provided between the particle 4a and the particle 4b. The particle 4a and the particle 4b may be in contact with each other. In such a case, the distance Ga is zero.

A distance Gb between the particle 4b and the particle 4c is smaller than the size db of the particle 4b. The distance Gb between the particle 4b and the particle 4c is smaller than the size Dc of the particle 4c. An empty space 6 is provided between the particle 4b and the particle 4c. The particle 4b and the particle 4c may be in contact with each other. In such a case, the distance Gb is zero.

Furthermore, a distance Gc between the particle 4a and the particle 4c is smaller than the size Da of the particle 4a. The distance Gc between the particle 4a and the particle 4c is smaller than the size Dc of the particle 4c. An empty space 6 is provided between the particle 4a and the particle 4c. The particle 4a and the particle 4c may be in contact with each other. In such a case, the distance Gc is zero.

In this manner, the large number of particles 4 in the porous portion 8 have a form in which a certain particle 4 is present very close to another particle 4, and an empty space 6 is present between the two particles that are present very close to each other.

The particle 4a and the particle 4b are bound to each other with a binder 5. The particle 4b and the particle 4c are bound to each other with the binder 5.

Each of the particles 4a, 4b, and 4c can contain an inorganic material. The inorganic material contained in each of the particles 4a, 4b, and 4c can be a material containing silicon and oxygen. The silicon and the oxygen may form a siloxane bond. The inorganic material contained in each of the particles 4a, 4b, and 4c may be silica.

Each of the particles 4a, 4b, and 4c may be a silica particle.

The binder 5 can contain an inorganic material. The inorganic material contained in the binder 5 can be a material containing silicon and oxygen. The silicon and the oxygen may form a siloxane bond. The inorganic material contained in the binder 5 may be a silicate.

Since the particles 4 and the binder 5 each contain an inorganic material, two particles each containing an inorganic material are bound to each other with the binder 5 containing an inorganic material.

In the example illustrated in FIG. 2A, the particles 4 (particles 4a, 4b, and 4c) can be hollow particles. More specifically, the particles 4 serving as hollow particles each have a shape in which a hollow portion 42 is covered with a solid shell 41. The shell 41 can contain the above-described inorganic material such as silica. In another example, the particles 4 (particles 4a, 4b, and 4c) can be solid particles. The particles 4 serving as solid particles may be formed of a uniform solid material. Alternatively, the particles 4 serving as solid particles may be configured to have a core-shell structure in which a solid core is covered with a solid shell.

The porous portion 8 can include an adhesion material 7 adhering to the particles 4. The adhesion material 7 can contain an organic material. The adhesion material 7 can be a residue of an organic material component contained in a coating liquid described later.

Figure 2B:
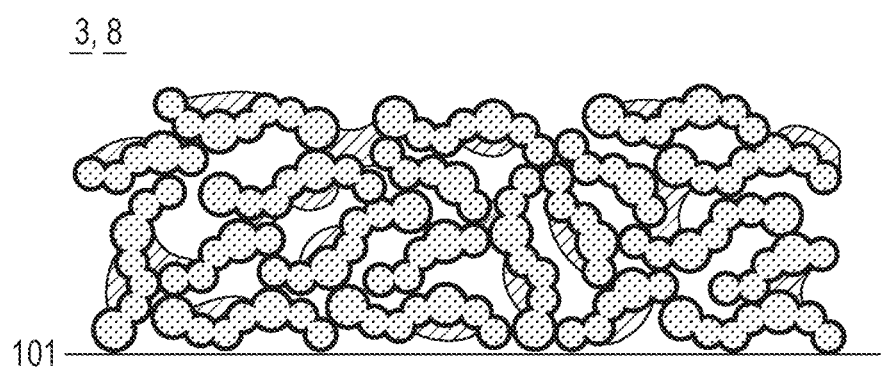

In an example illustrated in FIG. 2B, the particles 4 (particles 4a, 4b, and 4c) can be chain-like particles. That is, the particles 4 serving as chain-like particles have a shape in which a plurality of particles are linked together. An empty space 6 is provided between two chain-like particles.

The light-transmitting member 1 is required to have a high light transmittance. For example, the light transmittance of the light-transmitting member 1 is preferably 95.0% or more, and more preferably 99.0% or more. For example, an average transmittance of the light-transmitting member 1 in a wavelength region of 400 nm or more and 700 nm or less is preferably 95.01% or more, and more preferably 99.0/o or more. Furthermore, the transmittance at all wavelengths in a wavelength region of 400 nm or more and 700 nm or less is also preferably 95.0% or more, and more preferably 99.0% or more.

Figure 3A:
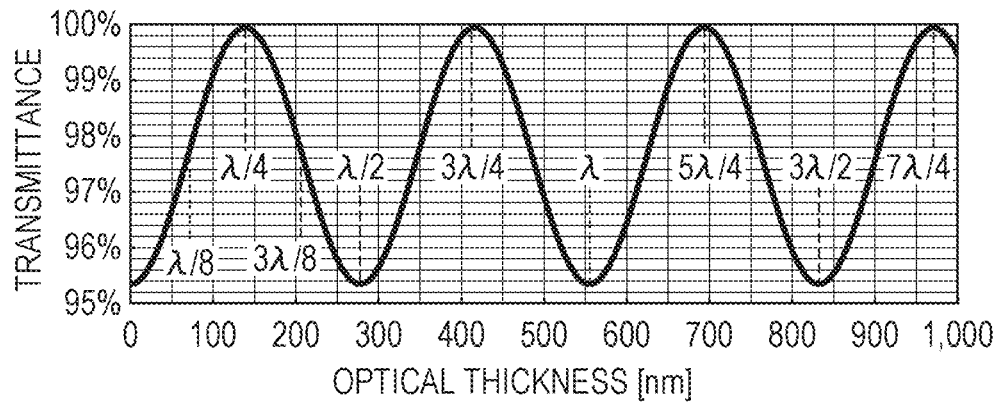
FIGS. 3A to 3C are each a schematic view illustrating the transmittance of a light-transmitting member, according to the subject disclosure.

FIG. 3A shows an example of the schematic relationship between the optical thickness of the functional film 3 and the transmittance of the light-transmitting member 1 with respect to light having a wavelength $\lambda$. When the optical thickness nd is an even multiple of $\lambda/4$ (nd=$\lambda/2$, $\lambda$, or $3\lambda/2$), the transmittance can be the same as that in the case where the functional film 3 is not provided (nd=0). When the optical thickness nd is an odd multiple of $\lambda/4$ (nd=$\lambda/4$, $3\lambda/4$, $5\lambda/4$, or $7\lambda/4$), the transmittance with respect to light having a wavelength of h can be increased as much as possible. However, the model shown in FIG. 3A does not consider the absorption and scattering of light in the functional film 3. In reality, as the thickness of the functional film 3 increases, the absorption and scattering of light in the functional film 3 of the light-transmitting member 1 increase, which may result in a decrease in the transmittance. Accordingly, the functional film 3 may have a smaller thickness. The optical thickness nd of the functional film 3 is preferably less than a half of a wavelength $\lambda$ (nd<$\lambda/2$) where $\lambda$ denotes a wavelength of target light for which the transmittance is measured. When the optical thickness nd is less than $\lambda/2$, the transmittance can be increased by providing the functional film 3. In particular, the optical thickness nd of the functional film 3 is preferably $\lambda/8$ or more and $3\lambda/8$ or less of the wavelength $\lambda$.

Next, the wavelength $\lambda$ will be described. The wavelength $\lambda$ is preferably 464 nm or more and 653 nm or less. This is due to the fact that the photopic standard luminosity factor with respect to light having a wavelength of 464 nm or more and 653 nm or less is 0.1 or more. By increasing the transmittance with respect to light having a wavelength at which the photopic standard luminosity factor is 0.1 or more, the recognition of reflected light by humans can be reduced. The wavelength $\lambda$ is more preferably 509 nm or more and 614 nm or less. This is due to the fact that the photopic standard luminosity factor with respect to light having a wavelength of 509 nm or more and 614 nm or less is 0.5 or more. By increasing the transmittance with respect to light having a wavelength at which the photopic standard luminosity factor is 0.5 or more, the recognition of reflected light by humans can be more effectively reduced. In the example in FIG. 3A, the wavelength $\lambda$ is set to 555 nm. This is due to the fact that the wavelength $\lambda$ at which the standard luminosity factor becomes 1.0, which is the highest value, is 555 nm.

Figure 3B:
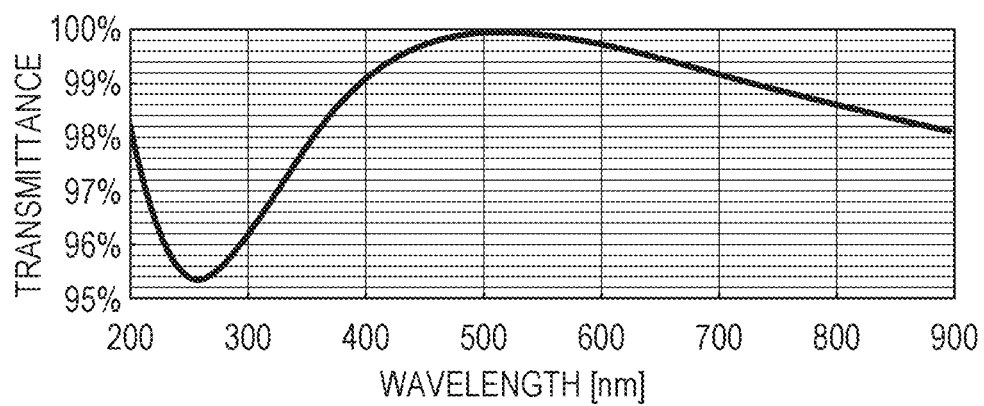

FIG. 3B shows an example of a schematic relationship of the transmittance of the light-transmitting member 1 with respect to light having various wavelengths. The example in FIG. 3B shows a case where the refractive index of the functional film 3 is 1.22 (the square root of the refractive index of the substrate 2), the physical thickness of the functional film 3 is 105 nm, and the optical thickness of the functional film 3 is 128 nm. In this case, the transmittance becomes maximum with respect to light having a wavelength of 512 nm in visible light. Specifically, this is the same as the case where the wavelength $\lambda$ is 512 nm. In the example in FIG. 3B, the transmittance at all wavelengths in the wavelength region of 400 nm or more and 700 nm or less is 99.0% or more. Thus, it is possible to provide a light-transmitting member 1 with which humans are less likely to recognize a reflection component of visible light.

Furthermore, in the example in FIG. 3B, the transmittance in the near-ultraviolet light (200 to 380 nm) is lower than the transmittance in the visible light (400 to 700 nm). Such transmission characteristics can realize UV protection effects and can provide the effect of reducing sunburn when the light-transmitting member is used as a face shield described later.

Figure 3C:
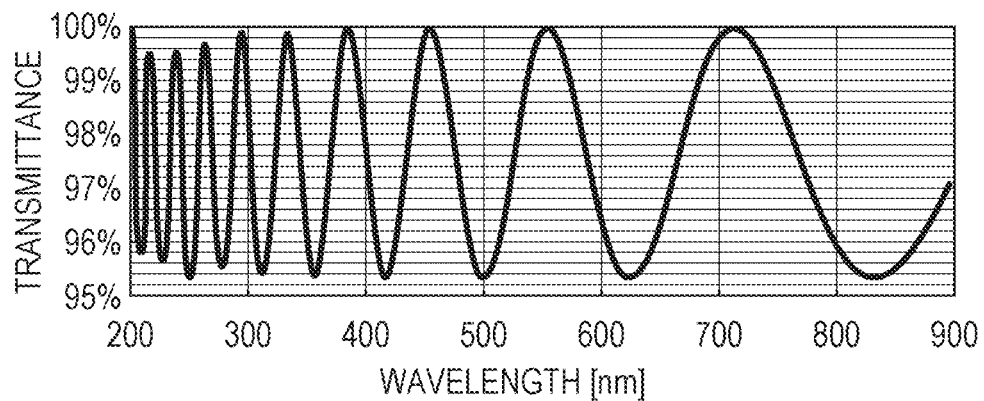

FIG. 3C also shows an example of a schematic relationship of the transmittance of the light-transmitting member 1 with respect to light having various wavelengths. The example in FIG. 3C shows a case where the refractive index of the functional film 3 is 1.22 (the square root of the refractive index of the substrate 2), the physical thickness of the functional film 3 is 1,023 nm, and the optical thickness of the functional film 3 is 1,248 nm. In this case, the transmittance becomes maximum with respect to light having a wavelength of 555 nm in visible light. Specifically, this means that the wavelength $\lambda$ is 555 nm, and the optical thickness nd is 9V14. As is understood from FIG. 3C, the transmittance significantly varies depending on the wavelength in the wavelength region of 400 nm or more and 700 nm or less, and the average transmittance does not exceed 99.0%, unlike the case in FIG. 3B. The comparison between FIG. 3B and FIG. 3C also shows that the optical thickness nd of the functional film 3 is preferably less than a half of the wavelength $\lambda$ (nd<$\lambda/2$).

The refractive index of the functional film 3 may be lower than the refractive index of the substrate 2. Assuming that a medium on the functional film 3 is air having a refractive index of 1.0, the functional film 3 can function as an antireflection film that reduces reflection of light between the medium and the substrate 2. As the refractive index of the functional film 3 is close to the square root of the refractive index of the substrate 2, the antireflection effect is further improved. A typical refractive index of the substrate 2 having the resin layer 11 is 1.45 to 1.65. Accordingly, the refractive index of the functional film 3 is preferably 1.20 or more and 1.30 or less, and more preferably 1.20 or more and 1.24 or less. At a high ratio of the empty space 6 included in the porous portion 8, the functional film 3 can have a refractive index of less than 1.20. However, at a high ratio of the empty space 6 included in the porous portion 8, the porous portion 8 of the functional film 3 may have insufficient wear resistance. At a refractive index of more than 1.30, a sufficient antireflection effect between the medium (air) and the substrate 2 may not be obtained.

The contact angle of water with respect to the front surface 110 on the functional film 3 in the light-transmitting member 1 is preferably less than 900. The same also applies to the back surface 120. At a contact angle of water of less than 90°, the light-transmitting member 1 is hydrophilic, and thus water droplets adhering to the front surface 110 can be made less likely to be visually recognized. In addition, fogging caused by fine water droplets can also be reduced, and an antifogging effect can be provided. To realize this function, the contact angle of water with respect to the front surface 110 on the functional film 3 is preferably 60° or less, more preferably 45° or less, and still more preferably 30° or less. If binding between the particles 4 is weak and the porous portion 8 has insufficient wear resistance, the contact angle of water tends to exceed 45°. Specifically, the contact angle can be defined as a contact angle of pure water at a room temperature of 23° C. and a humidity of 40% to 45% RH. The contact angle of water is preferably 30 or more, and more preferably 5° or more. If the contact angle of water is less than 3°, for example, moisture tends to enter the functional film 3 from the front surface 110 or the back surface 120 of the functional film 3, and environmental stability may decrease.

The thickness Ta of the porous portion 8 is larger than the sum of the size Da of the particle 4a and the size db of the particle 4b (Ta>Da+db). In this example, three particles 4a, 4b, and 4c are stacked in the film thickness direction of the functional film 3. However, since the centers of the particles are shifted relative to each other, the thickness Ta of the porous portion 8 is smaller than the sum of the size Da of the particle 4a, the size db of the particle 4b, and the size De of the particle 4c (Ta<Da+Db+Dc).

The size Da of the particle 4a, the size db of the particle 4b, and the size Dc of the particle 4c are each, for example, 1 nm or more, and, for example, 10 nm or more. The size Da of the particle 4a, the size db of the particle 4b, and the size Dc of the particle 4c are each, for example, less than 1 μm, for example, less than 500 nm, for example, less than 300 nm, and, for example, less than 100 nm. As the size of the particles 4 decreases, the size of the empty spaces 6 between the particles 4 decreases. As the size of the empty spaces 6 between the particles 4 increases, the refractive indices of the porous portion 8 and the functional film 3 can be lowered. On the other hand, as the size of the particles 4 decreases, the difference in height of the surface of the porous portion 8 or the functional film 3 also decreases. When the functional film 3 has a small difference in height of the surface thereof, light scattering on the surface of the functional film 3 can be reduced.

Incidentally, bacteria have a size of about 1 to 5 μm. If bacteria adhere to the light-transmitting member 1, the bacteria can proliferate on the light-transmitting member 1. When the size of the particles 4 is less than 1 μm, the size of the empty spaces 6 and the difference in height of the surface of the functional film 3 can be reduced to such an extent that the proliferation of bacteria in the porous portion 8 and on the porous portion 8 (on the functional film 3) is certainly suppressed.

Viruses have a size of about 20 to 300 nm. If viruses adhere to the light-transmitting member 1, the viruses can be carried on the light-transmitting member 1. When the size of the particles 4 is substantially the same as or smaller than the size of the viruses, the size of the empty spaces 6 and the difference in height of the surface of the functional film 3 can be reduced to such an extent that the carrying of viruses on the light-transmitting member 1 is certainly suppressed. For example, the size of corona viruses of such as COVID-19 (SARS-CoV-2) and influenza viruses is about 100 nm. When the size of the particles 4 is less than the size of these viruses (less than 100 nm), the size of the empty spaces 6 and the difference in height of the surface of the functional film 3 can be reduced to such an extent that the carrying of the viruses on the light-transmitting member 1 is certainly suppressed. Accordingly, the size Da of the particle 4a, the size db of the particle 4b, and the size Dc of the particle 4c may be smaller than that of corona viruses of such as COVID-19 (SARS-CoV-2) and influenza viruses.

The formation of the functional film 3 can provide the light-transmitting member 1 with an antistatic function. For example, when the particles 4 and the binder 5 contain an inorganic material having a siloxane bond, hydroxyl groups present on a solid surface of the porous portion 8 adsorb moisture in air. This decreases the electrical resistance to reduce charging of the front surface 110 or the back surface 120 of the light-transmitting member 1. Therefore, it is possible to reduce foreign substances such as dust adhering to the light-transmitting member 1 due to static electricity.

The resin layer 11 of the substrate 2 of the light-transmitting member 1 is not particularly limited as long as the resin layer 11 has good processability and has transparency for ensuring visibility. Examples of specific resins include polyester resins such as polyethylene terephthalate (PET) and polybutylene terephthalate (PBT); polycarbonate (PC) resins, triacetate cellulose (TAC) resins, cycloolefin (COP) resins, polymethyl methacrylate (PMMA) resins, and acrylic polyvinyl alcohol (PVA) resins. Of these, amorphous resins having good transparency and adhesion can be used as the resin that forms the resin layer 11 of the substrate 2. However, even when the substrate 2 is formed of a crystalline resin, the functional film 3 of this embodiment can realize sufficient functionality because the functional film 3 can improve the transmittance and conform to flexibility of the substrate 2. Since crystalline resins have higher chemical resistance than amorphous resins, crystalline resins are less likely to cause a limitation in the formation of the functional film 3. Main crystalline resins are polyethylene (PE), polypropylene (PP), polyamides (PA), polyacetal, polyoxymethylene (POM), polyethylene terephthalate (PET), polybutylene terephthalate (PBT), polyphenylenesulfide (PPS), polyether ether ketones (PEEK), liquid crystal polymers (LCP), and polytetrafluoroethylene (PTFE). Polycarbonate (PC) resins and polymethyl methacrylate (PMMA) resins are amorphous resins. The resin layer 11 is suitably formed of a polyester resin, and particularly preferably formed of polyethylene terephthalate (PET).

The resin layer 11 may be formed of a raw material that does not include particles. The design of the raw material that does not include particles can reduce scattering due to raw material particles in the resin layer 11 and can provide a substrate 2 having good visibility with high light transmittance.

The distance between the resin layer 11 and the porous portion 8 is smaller than the thickness Ta of the porous portion 8. The substrate 2 may have a layer other than the resin layer 11. The distance between the resin layer 11 and the porous portion 8 may be zero. In the example in FIG. 1B, intermediate layers 12 are disposed between the resin layer 11 and the corresponding porous portion 8. The intermediate layers 12 each have a function of improving adhesion between the substrate 2 and the functional film 3. Thicknesses Te and Tf of the intermediate layers 12 are smaller than the thicknesses Ta and Tc of the functional films 3, respectively, disposed on the intermediate layers 12 (Te<Ta, and Tf<Tc). The thicknesses Te and Tf of the intermediate layers 12 are each smaller than a thickness Td of the resin layer 11 disposed under the intermediate layers 12 (Te<Td, and Tf<Td). The thicknesses Te and Tf of the intermediate layers 12 can each be 1 nm to 100 nm. In addition, in order to improve adhesiveness to the corresponding functional film 3, the main surfaces 101 and 102 of the substrate 2 may be subjected to, for example, adhesion-improving treatment or UV ozone, plasma, or corona treatment.

Figure 1C:
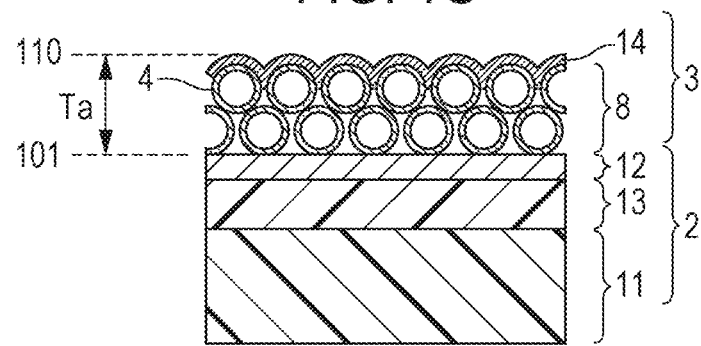

In an example in FIG. 1C, a hard-coat layer 13 is disposed between a resin layer 11 and an intermediate layer 12. The thickness of the hard-coat layer 13 may be smaller than the thickness Td of the resin layer 11 disposed under the hard-coat layer 13. A typical hard-coat layer can be a resin layer. The substrate 2 has a thickness of 1 µm or more and less than 1 mm. If the thickness of the substrate 2 is less than 1 µm, formability of a functional film 3 may be degraded. Reducing the thickness of the substrate 2 is advantageous to improve the light transmittance of the light-transmitting member 1. If the thickness of the substrate 2 is 1 mm or more, processability such as cutting of the substrate 2 is degraded. The thickness of the substrate 2 is preferably 100 µm or more and less than 250 µm.

In the example in FIG. 1C, a functional film 3 includes a protective layer 14 covering a porous portion 8. The functional film 3 may realize a desired function only by the porous portion 8 but may have a function added by the protective layer 14. The protective layer 14 may function as, for example, a particle-fixing layer that reduces detachment of particles 4 of the porous portion 8. Alternatively, the protective layer 14 may function as a hard-coat layer that reduces scratching on the light-transmitting member 1. The protective layer 14 may be an electroconductive layer that provides the surface of the functional film 3 with conductive properties. In such a case, the protective layer 14 can provide the light-transmitting member 1 with a charging suppression function. The protective layer 14 may have a function of enhancing hydrophilicity or hydrophobicity of the functional film 3. For example, in the case of providing the functional film 3 with hydrophilicity, if the functional film 3 having only the porous portion 8 has a contact angle of water of 45° to 90°, a hydrophilic protective layer 14 can be added to the functional film 3 so that the contact angle of water on the front surface 110 of the light-transmitting member 1 is 45° or less.

Figure 4A:
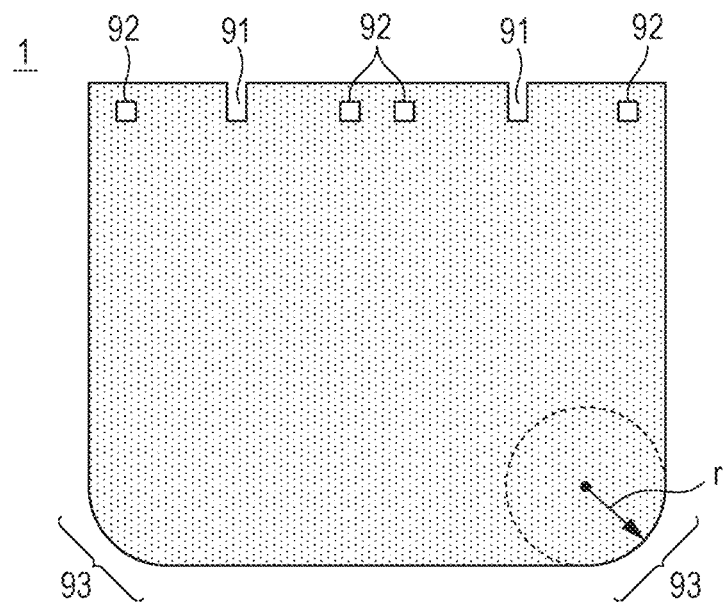
FIG. 4A is a schematic view illustrating an example of a light-transmitting member, according to the subject disclosure.

FIG. 4A illustrates an example of the shape of a light-transmitting member 1. The light-transmitting member 1 in FIG. 4A has a maximum width of 2 cm or more and 2 m or less. The maximum width of the light-transmitting member 1 may be 10 cm or more and 1 m or less and may be 20 cm or more and 50 cm or less. The light-transmitting member 1 has at least one of notches 91 and holes 92. The notches 91 and/or the holes 92 are used for holding the light-transmitting member 1. Since the light-transmitting member 1 is held by the notches 91 and/or the holes 92, the replacement of the light-transmitting member 1 can be facilitated.

The outer periphery of the light-transmitting member 1 includes curved portions 93 each having a radius r of curvature of 1 mm or more. The formation of the curved portions 93 can reduce the possibility that the outer periphery of the light-transmitting member 1 damages another object.

Figure 4B:
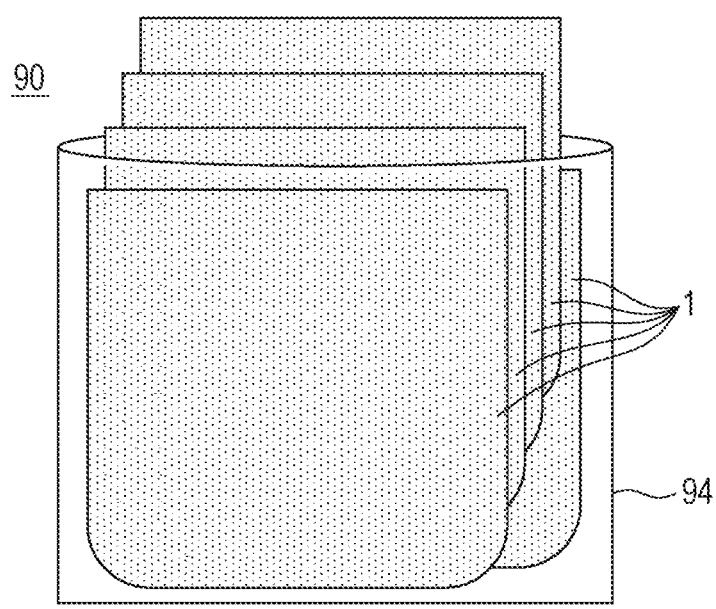
FIG. 4B is a schematic view illustrating an example of a package unit, according to the subject disclosure.

FIG. 4B illustrates an example of a package unit 90. The package unit 90 includes at least three (five, in this example) light-transmitting members 1 that overlap one another, and a package 94 that contains the at least three (five, in this example) light-transmitting members 1. The preparation of this package unit 90 enables a light-transmitting member 1 with less degradation to be used at least three times. A used light-transmitting member 1 can also be replaced with a light-transmitting member 1 with less degradation. Since a functional film 3 of each light-transmitting member 1 in which particles 4 are bound together with a binder 5 has a sufficient strength, damage on the functional film 3 of the light-transmitting member 1 sandwiched between two light-transmitting members 1 is suppressed. In addition, when the functional film 3 is provided with an antistatic function, it is possible to suppress the phenomenon that light-transmitting members 1 overlapping one another are adsorbed by static electricity, and thus the light-transmitting members 1 are easily taken out from the package 94.

A method for manufacturing a light-transmitting member 1 includes a step of applying a coating liquid for forming a porous portion 8 to a substrate 2 to form a coating film, and a step of drying and/or baking the substrate 2 on which the coating film has been formed to form the porous portion 8.

Examples of the method for applying the coating liquid include a gravure coating method, a die coating method, a spin coating method, a blade coating method, a roll coating method, a slit coating method, a printing method, and a dip coating method. When a light-transmitting member having a three-dimensionally complex shape, such as a concave surface, and a thin film is manufactured, a gravure coating method is preferable from the viewpoints of application to a large area and the uniformity of the film thickness. Micro-gravure coating with which a thin film can be formed in the order of 100 nm is more preferable. In particular, for coating on a roll-shaped long film, roll-to-roll micro-gravure coating is preferable.

To form a porous portion 8, a coating liquid is applied to a substrate 2, and drying and/or baking is performed. The drying and/or baking is a step of removing a solvent and depositing particles 4 while the particles 4 are bound to each other without disturbing the arrangement thereof to form a porous portion 8. The temperature of the drying and/or baking is preferably 20° C. or higher and 200° C. or lower, although it depends on the heat resistance temperature of the substrate 2. The time of the drying and/or baking may be determined such that the organic solvent in the layer can be evaporated without influence on the substrate 2 and is preferably 10 minutes or more and 200 hours or less, and more preferably 30 minutes or more and 24 hours or less.

To obtain a porous portion 8 in which the particles 4 are highly arranged, the arrangement of the particles 4 is preferably well ordered. The difference in arrangement of the particles 4 mainly depends on the dispersion state of the particles 4 in the coating liquid for forming a porous portion 8 and the dispersion state of the particles 4 during the formation of the coating film.

When the particles 4 in the coating liquid are sufficiently dispersed without influence of a dispersion medium or a binder 5, the particles 4 are easily arranged. However, when the particles 4 are dispersed in a slightly aggregated state due to the influence of a dispersion medium or a binder 5, the arrangement is deteriorated.

Furthermore, when the coating liquid is applied to the substrate 2 and a coating film is formed, volatilization and drying of a solvent and flowing of the particles 4 due to condensation also significantly affect the arrangement. Even in a good dispersion state of the particles 4 in the coating liquid, if the particles 4 are aggregated during drying in the formation of a coating film, the arrangement of the particles 4 are disturbed. Consequently, the gaps between the particles 4 are increased in the resulting coating film, and the size of voids in the planar direction of the substrate 2 is increased. Therefore, scattering is increased in visible light. Furthermore, since the coating film is formed in a state where the particles 4 are deposited not in an aligned manner but in a shifted manner, the stress distribution of the coating film is uneven, and the strength of the film is not sufficiently maintained.

If the arrangement of the particles 4 is poor, voids having a size of several tens of nanometers tend to be formed. It is assumed that, in contrast, if the particles 4 are highly arranged, the size of the empty spaces 6 of the porous portion 8 is decreased, and an invasion of viruses into the inside of the light-transmitting member 1 can also be thereby suppressed. The size of viruses is about 1/1000 of the size of bacteria and is several tens of nanometers. In a case of a hydrophilic light-transmitting member 1, even if viruses adhere to the light-transmitting member 1, the viruses can be probably easily washed away with water.

As described above, the use of particles 4 to which a surface treatment agent (adhesion material 7) is added enables a coating film of the porous portion 8 to be formed in a state where the particles 4 are deposited in an aligned manner without disturbing the arrangement thereof.

The surface treatment agent included in the porous portion 8 can be determined by, for example, elementary analysis in the particles 4 or the porous portion 8 or separation quantitative analysis such as ion-exclusion chromatography.

Examples of the shape of the particles 4 include a spherical shape, a cocoon-like shape, a barrel-like shape, a disk shape, a rod shape, an acicular shape, a rectangular shape, and a chain-like shape. In particular, the particles 4 may be hollow particles having a spherical shell and a hollow portion inside the spherical shell, or chain-like particles which are connected hydrophilic particles.

The hollow particles can lower the refractive index of the porous portion 8 due to a gas (refractive index: 1.0) included in the hollow portions thereof. The hollow portion may have either a single pore or multiple pores, which can be appropriately selected. Hollow particles can be manufactured by, for example, a method disclosed in Japanese Patent Laid-Open No. 2001-233611 or a method disclosed in Japanese Patent Laid-Open No. 2008-139581. Hollow particles can lower the refractive index of a layer in which particles 4 that are aligned in a parallel direction with respect to a surface of the substrate 2 are stacked so as to form a plurality of layers.

The binder 5 may be formed of an inorganic material such as a silicate. Since the binder 5 does not substantially contain a resin which is an organic polymer, and the particles 4 formed of an inorganic material (silica) are bound together with the binder 5 formed of, for example, an inorganic material (silicate), a porous portion 8 having a low refractive index and high strength can be formed.

This manufacturing method can provide a light-transmitting member 1 that is less affected by reflection and glare and that has good visibility while maintaining a low refractive index. The porous portion 8 of the light-transmitting member 1 is formed by uniformly applying a dispersion liquid of silica particles and realizes a functional film 3 having a low refractive index. The porous portion 8 has a feature that the porous portion 8 itself has a low refractive index because the porous portion 8 has empty spaces 6 therein and pores inside the particles 4. In addition, when a binder 5 formed of an inorganic material is used for binding the particles 4 to each other, the refractive index can be made lower than that of a porous portion 8 formed by using a binder 5 formed of a resin material. If a binder 5 (binder resin) formed of a resin material is used, a high resin content in the porous portion 8 increases the refractive index of the functional film 3, resulting in an increase in reflection. In addition, during volatilization of an organic solvent in a coating composition, the particles 4 are bound to the binder resin, and thus the particles 4 tend to aggregate. The organic solvent in the coating composition rapidly volatilizes on the surface side of the coating film. Accordingly, even if the formation of irregularities of the particles 4 can be suppressed on the surface of the coating film, on which drying rapidly proceeds, the arrangement of the particles 4 inside the coating film can be deteriorated. Therefore, the use of a binder resin makes it difficult to further improve antireflection and transparency. Accordingly, there is a problem in that sufficient visibility cannot be ensured because of the influence of reflection and glare due to external light such as a fluorescent lamp.

Furthermore, since the functional film 3 having a low refractive index is disposed on both surfaces of the substrate 2, scattering from the main surfaces 101 and 102 of the substrate 2 can be cancelled. The use of the light-transmitting member 1 can improve visibility in a wide range of field of view. Accordingly, it is possible to provide a light-transmitting member that realizes a better antireflection function and high transparency and that has good visibility.

Figure 5A:
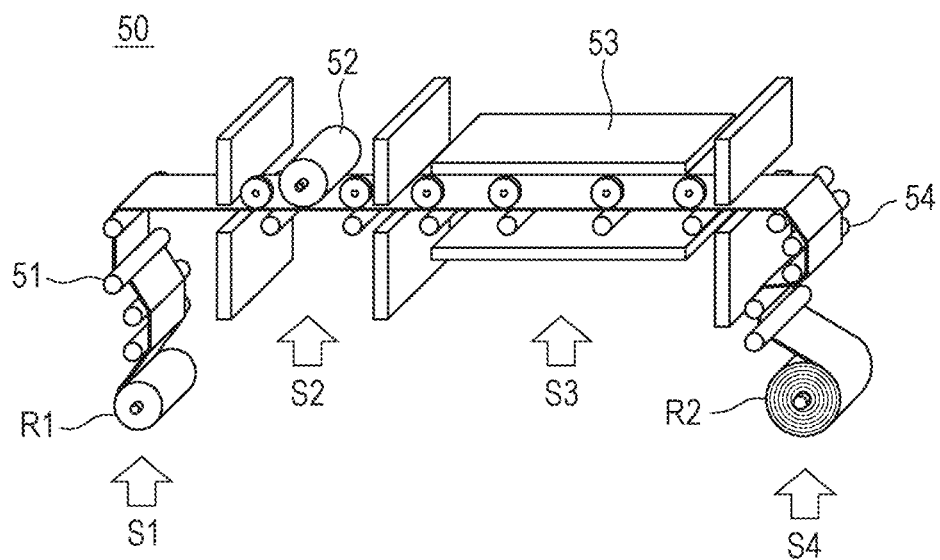
FIG. 5A is a schematic view illustrating an example of a method for manufacturing a light-transmitting member, according to the subject disclosure.

FIG. 5A is a schematic view illustrating an example of a method for manufacturing a light-transmitting member 1. FIG. 5A is a schematic view illustrating a manufacturing method using a roll-to-roll film-forming apparatus 50, which is an example of the method for manufacturing a light-transmitting member 1. A wound body (roll) R1 formed of a substrate 2 that is wound is provided. Subsequently, the wound body R1 is placed on an unwinding unit 51 of the film-forming apparatus 50. In step S1, the substrate 2 of the wound body R1 is unwound by the unwinding unit 51 and is spread to a coating unit 52 of the film-forming apparatus 50. In step S2, a coating liquid is applied to the spread substrate 2 with a roll coater of the coating unit 52. The roll coater is, for example, a gravure coater, a reverse coater, a slot-die coater, a lip coater, a blade coater, a bar coater, or an air knife coater. In step S3, the substrate 2 is fed from the coating unit 52 to a drying unit 53 of the film-forming apparatus 50, and the resulting coating film is dried by a heater of the drying unit 53. In this manner, a functional film 3 is formed on the spread substrate 2 by a wet film-forming method. In step S4, the substrate 2 on which the functional film 3 has been formed is fed from the drying unit 53 to a winding unit 54 of the film-forming apparatus 50 and is wound by the winding unit 54. As a result, a wound body (roll) R2 of a light-transmitting member 1 can be obtained.

Figure 5B:
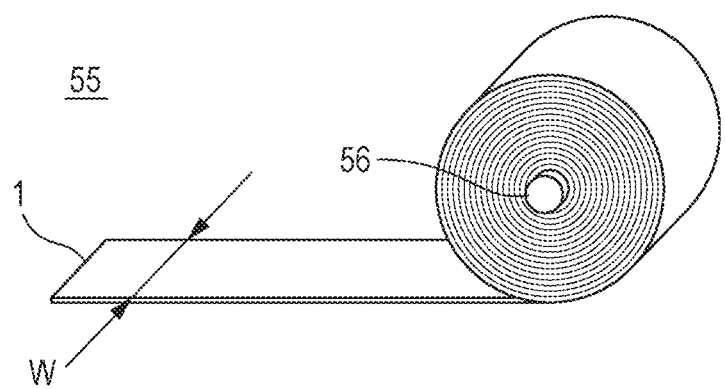
FIG. 5B is a schematic view illustrating an example of a wound body, according to the subject disclosure.

FIG. 5B is a schematic view illustrating an example of a wound body (roll). A wound body 55 includes a light-transmitting member 1 and a core 56. A length of the long side of the light-transmitting member 1 is 10 m or more, and the light-transmitting member 1 is wound around the core 56. A length W of the short side of the light-transmitting member 1 may be 2 m or less and may be 20 cm or more. Such a wound body 55 is advantageous to distribute a light-transmitting member 1 having a large area. In addition, a large number of light-transmitting members 1 each having a maximum width L of 2 cm or more and 2 m or less, as illustrated in FIG. 4A, can be manufactured by spreading and cutting a light-transmitting member 1 of such a wound body 55.

The light-transmitting member 1 can be used as a shield. The demand for shields such as a shield partition and a face shield for the purpose of preventing the spread of infection has been increasing due to the influence of a novel coronavirus (COVID-19 (SARS-CoV-2)). In particular, in medical institutions, from the viewpoints of strengthening infection control and providing advanced medical treatment, a highly transparent and low-reflective face shield having good visibility has been desired, and improvement in the functionality of a light-transmitting member using a resin substrate has been desired.

Figure 6A:
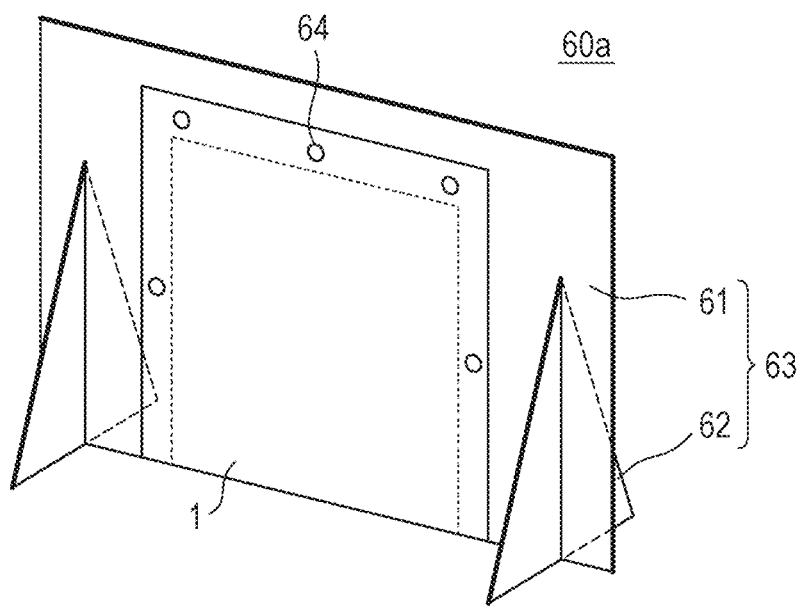
FIGS. 6A and 6B are each a schematic view illustrating an example of a shield, according to the subject disclosure.

FIG. 6A is a schematic view illustrating a shield partition 60a which is an example of a shield. The shield partition 60a includes a light-transmitting member 1 and a holder 63 that holds the light-transmitting member 1. The holder 63 includes a fixing portion 61 to which the light-transmitting member 1 is fixed and support portions 62 for stably installing the fixing portion 61 on a ground contacting surface. The support portions 62 are connected to the fixing portion 61. The fixing portion 61 has a frame shape having an opening, and the light-transmitting member 1 is disposed in the opening. A peripheral edge portion of the light-transmitting member 1 is fixed to the fixing portion 61 with fixing parts 64 such as pins or screws. The fixing parts 64 can pass through the notches 91 and the holes 92 illustrated in FIG. 4A. The support portions 62 function as legs and support the fixing portion 61. The shield partition 60a can be disposed on, for example, a table or a counter. The shield partition 60a may be provided with a ventilation fan for ventilating the atmosphere adjacent to the light-transmitting member 1.

Figure 6B:
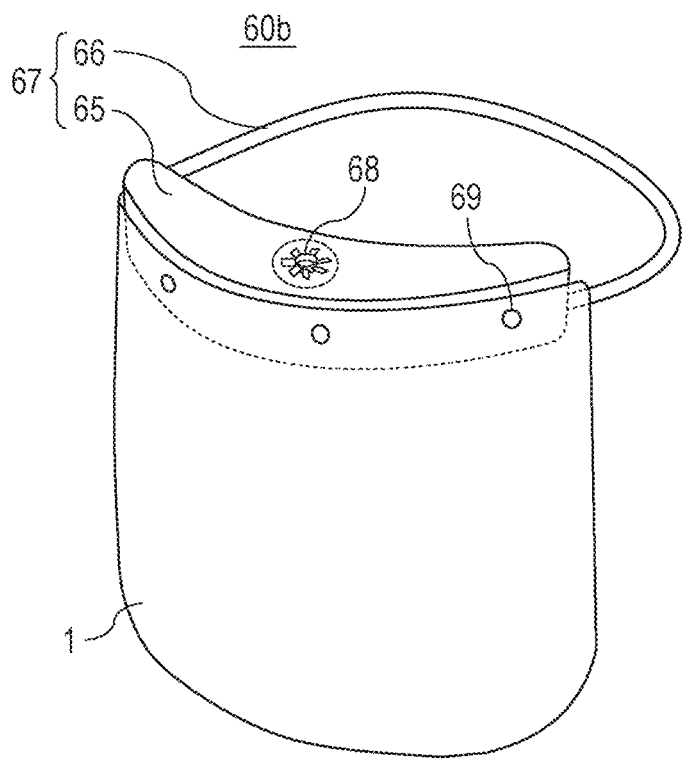

FIG. 6B is a schematic view illustrating a face shield 60b which is an example of a shield. The face shield 60b includes a light-transmitting member 1 and a holder 67 that holds the light-transmitting member 1. The holder 67 has a structure configured to fix the light-transmitting member 1 to a user such that the light-transmitting member 1 covers at least part of the face of the user. The holder 67 includes a fixing portion 65 to which the light-transmitting member 1 is fixed and a support portion 66 for fixing the fixing portion 65 to the user. The support portion 66 is connected to the fixing portion 65. The fixing portion 65 is rod-like, and a peripheral edge portion of the light-transmitting member 1 is fixed to a side face of the fixing portion 65 with fixing parts 69 such as pins or screws. The fixing parts 69 can pass through the notches 91 and/or the holes 92 illustrated in FIG. 4A. The belt-like support portion 66 is worn by a wearer to support the fixing portion 65. The light-transmitting member 1 of the face shield 60b covers, for example, at least any of the eyes, nose, and mouth of the user and may cover all of them.

The surface of the light-transmitting member 1 can have a curved surface. The curved surface of the light-transmitting member 1 may be formed along the face, and the radius of curvature of the curved surface is preferably 10 cm or more. The outer surface (the surface opposite to the face side) of the light-transmitting member 1 in the face shield 60b can be a front surface 110, and the inner surface (the surface on the face side) can be a back surface 120. The functional film 3 may be provided on both surfaces of the light-transmitting member 1. When the face shield 60b is used, scratches on the outer surface are more likely to occur than that on the inner surface. Accordingly, considering the scratch resistance of the light-transmitting member 1, it is also effective to make the thickness of the functional film 3 on the outer surface side larger than that of the functional film 3 on the inner surface side. When the functional film 3 is provided on only one surface (the front surface 110) of the light-transmitting member 1, the front surface 110 of the functional film 3 may be the inner surface (the surface on the face side), or the front surface 110 of the functional film 3 may be the outer surface (the surface opposite to the face side). When the antifogging function due to hydrophilicity of the functional film 3 is expected, the functional film 3 may be provided on the inner surface side. When the antireflection effect of the functional film 3 is expected, the functional film 3 may be provided on the outer surface side because a light source on the outer surface side can be a main factor of reflected light.

The face shield 60b may be provided with a ventilation fan 68 configured to ventilate the atmosphere adjacent to the light-transmitting member 1. In this example, the ventilation fan 68 is provided inside the holder 67 (fixing portion 65). In manufacturing of articles, a wearer wearing such a face shield 60b may assume a role of observing a product and/or a manufacturing apparatus through the light-transmitting member 1. According to a method for manufacturing an article, the use of the face shield 60b can not only protect the face of the wearer but also improve the quality of the article and the work efficiency owing to good visibility of the light-transmitting member 1.

Figure 7:
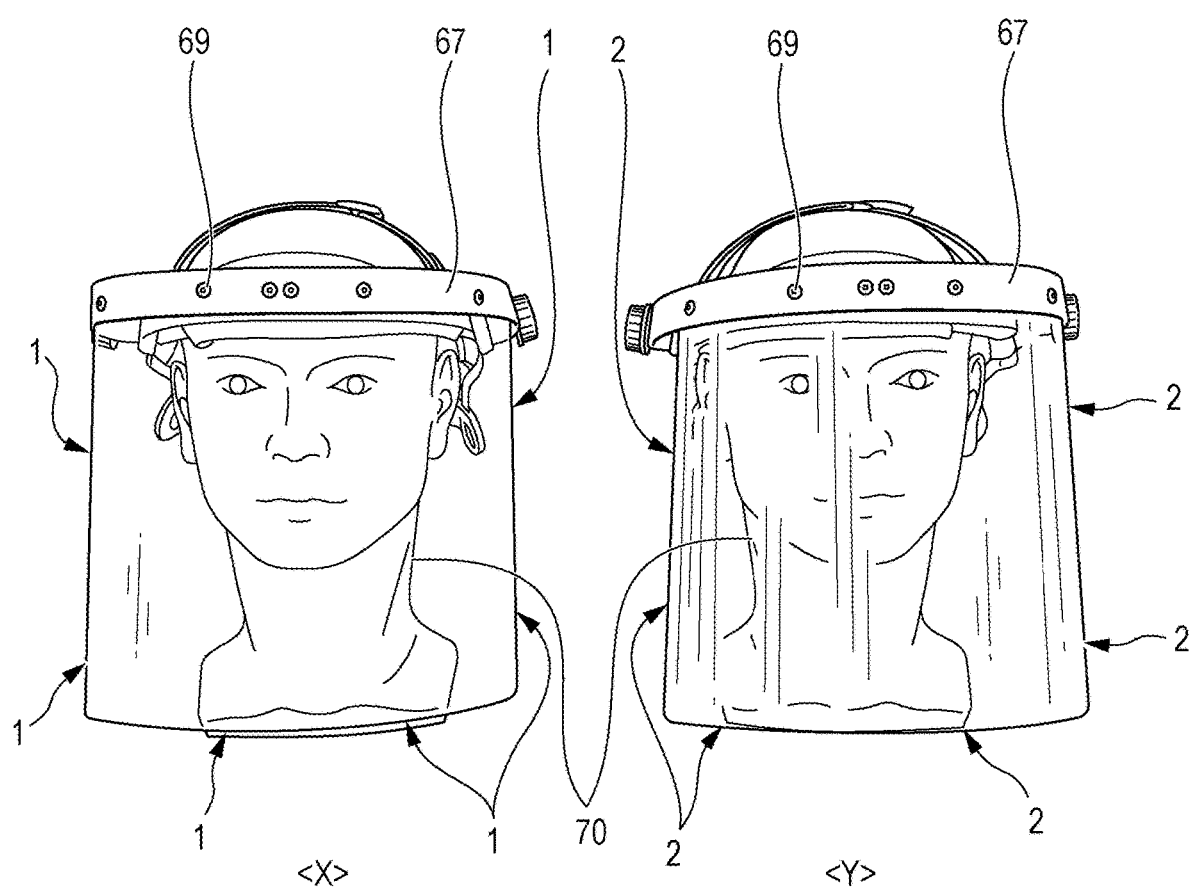
FIG. 7 is a schematic view illustrating an example of a shield, according to the subject disclosure.

FIG. 7 is a picture (photograph) produced by wearing face shields 60b as illustrated in FIG. 6B on objects 70 that resemble the heads, and capturing an image of the objects 70 through light-transmitting members 1. The face shield 60b that is worn on the object 70 on the left side X of the photograph in FIG. 7 includes a light-transmitting member 1 that includes a substrate 2 and a functional film 3 disposed on the substrate 2. The face shield 60b that is worn on the object 70 on the right side Y of the photograph in FIG. 7 includes a substrate 2 on which no functional film 3 is provided. Leading ends of arrows illustrated in FIG. 7 indicate the outer periphery of the light-transmitting member 1 or the substrate 2. Thus, the picture produced by capturing an image of the object 70 through the light-transmitting member 1 can satisfactorily express the object 70. Therefore, according to this method for producing a picture, a picture with high quality can be produced, and the satisfaction of the audience can be enhanced by distributing, broadcasting, or circulating such a picture with high quality.

From one side of a shield such as the shield partition 60a or the face shield 60b, the opposite side of the shield can be visually recognized through the light-transmitting member 1. Since the light-transmitting member 1 has a structure with an enhanced transmittance, the generation of reflected light in the light-transmitting member 1 can be reduced to improve visibility. Since the light-transmitting member 1 has a structure with an enhanced hydrophilicity, fogging due to water vapor can be reduced to improve visibility. Even when airborne water droplets such as water droplets adhere to the light-transmitting member 1, visibility of the water droplets can be reduced.

The user (wearer) of the shield can visually recognize the scenery through the light-transmitting member 1, and an observer other than the wearer can observe the face of the user through the light-transmitting member 1. In such a case, since the light-transmitting member 1 has a structure with an enhanced transmittance, the generation of reflected light in the light-transmitting member 1 can be reduced to improve visibility. When the functional film 3 with an enhanced hydrophilicity is provided on a face side of the light-transmitting member 1, fogging due to the exhaled air of the wearer can be reduced to suppress a decrease in visibility due to fogging. Even when airborne water droplets generated from the wearer adhere to the face side of the light-transmitting member 1, visibility of the water droplets from an observer other than the wearer is decreased by wettability of the light-transmitting member 1, and thus discomfort to the observer can be reduced. In the case where the functional film 3 with an enhanced hydrophilicity is provided on a side of the light-transmitting member 1 opposite from the face, even when airborne droplets (such as rain) toward the wearer adhere to the light-transmitting member 1, a decrease in visibility due to the water droplets can be suppressed.

As described above, the use of a shield including the light-transmitting member 1 can achieve objects other than the object of stopping the spread of infectious diseases.

Figure 8A:
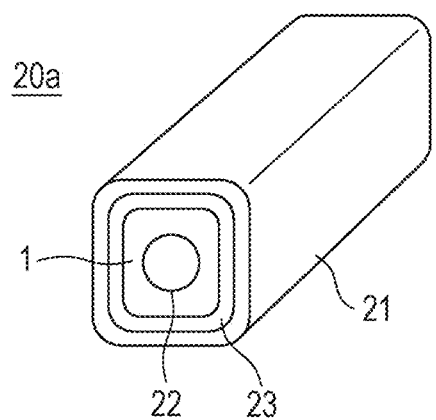
FIGS. 8A and 8B are each a schematic view illustrating an example of an apparatus, according to the subject disclosure.

FIG. 8A illustrates an imaging apparatus 20a which is an example of an apparatus including a light-transmitting member 1. The imaging apparatus 20a includes a body 21 that houses an imaging unit 22. A light-transmitting component 23 is disposed in front of the imaging unit 22. The light-transmitting component 23 is fixed to the body 21. The light-transmitting component 23 is a cover made of, for example, glass or a plastic. A light-transmitting member 1 is bonded to the outer surface of the light-transmitting component 23. A functional film 3 having a porous portion 8 is provided only on one main surface of a substrate 2 of the light-transmitting member 1, and a functional film 3 having a porous portion 8 is not provided on the other main surface of the substrate 2. An adhesive layer for bonding the substrate 2 to the light-transmitting component 23 is disposed on the other main surface of the substrate 2. The functional film 3 disposed on the light-transmitting member 1 can provide the imaging apparatus 20a with functionality such as antireflection, prevention of static charge, antifogging, and drip-proofness. Furthermore, when the imaging apparatus 20a is configured such that a degraded light-transmitting member 1 can be replaced with a light-transmitting member 1 with less degradation, the performance of the imaging apparatus 20a can be maintained for a long period of time.

Figure 8B:
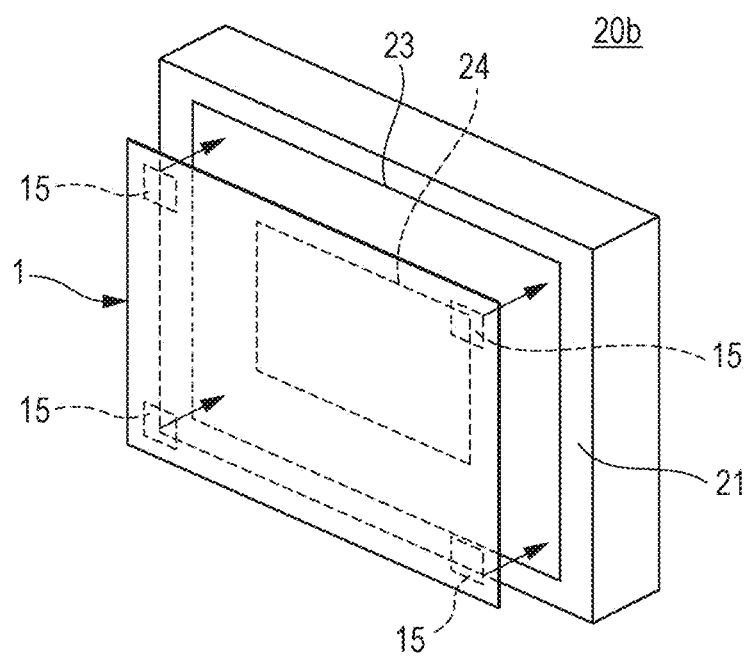

FIG. 8B illustrates a display apparatus 20b which is an example of an apparatus including a light-transmitting member 1. The display apparatus 20b includes a body 21 that houses a display unit 24. The display unit 24 can be formed by a display device or printed matter. A light-transmitting component 23 is disposed in front of the display unit 24. The light-transmitting component 23 is fixed to the body 21. The light-transmitting component 23 is a cover made of, for example, glass or a plastic. A light-transmitting member 1 is bonded to the outer surface of the light-transmitting component 23. A functional film 3 having a porous portion 8 is provided on each of the two main surfaces of a substrate 2 of the light-transmitting member 1. An adhesive layer 15 for bonding the substrate 2 to the light-transmitting component 23 is disposed on one of the main surfaces of the substrate 2. To enhance the adhesion between the adhesive layer 15 and the substrate 2, the functional film 3 is not provided between at least part of the adhesive layer 15 and the substrate 2. In this manner, the functional film 3 does not necessarily have to be provided on the entire main surface of the substrate 2, and the functional film 3 may be patterned on the substrate 2. The functional film 3 disposed on the light-transmitting member 1 can provide the display apparatus 20b with functionality such as antireflection, prevention of static charge, prevention of glare, antifogging, and drip-proofness. Furthermore, when the display apparatus 20b is configured such that a degraded light-transmitting member 1 can be replaced with a light-transmitting member 1 with less degradation, the performance of the display apparatus 20b can be maintained for a long period of time.

EXAMPLES

Example 1

A light-transmitting member was produced as described below.

A coating liquid for forming a functional film was prepared by blending components having the composition below. While 1-ethoxy-2-propanol (hereinafter abbreviated as 1E2P) was added to 580 g of an isopropyl alcohol dispersion liquid of hollow silicon oxide particles (THRULYA 1110, manufactured by JGC Catalysts and Chemicals Ltd., average particle size: about 50 nm, shell thickness: about 10 nm, solid content: 20.5% by mass), isopropyl alcohol was distilled off by heating. The isopropyl alcohol was distilled off until the solid content became 19.5% by mass to prepare 610 g of a 1E2P solvent-substituted liquid of the hollow silicon oxide particles (hereinafter referred to as a solvent-substituted liquid A). A surface treatment agent (heptafluorobutyric acid, manufactured by Tokyo Chemical Industry Co., Ltd.) was added to the prepared solvent-substituted liquid A such that a ratio of hollow silicon oxide particles to the surface treatment agent component was 100/1. Thus, a dispersion liquid B was prepared.

To another container, 11.4 g of 1-propoxy-2-propanol and 4.5 g of methyl polysilicate (methyl silicate 53A, manufactured by Colcoat Co., Ltd.) were gradually added and stirred at room temperature for 120 minutes to prepare a silica sol (hereinafter referred to as a silica sol 1).

The dispersion liquid B was diluted with ethyl lactate so as to have a solid content of 3.9% by mass. The silica sol 1 was then added to the dispersion liquid B such that a ratio of hollow silicon oxide particles to the silica sol component was 100/12. The resulting mixture was further mixed by stirring at room temperature for two hours to prepare a coating liquid C containing hollow silicon oxide particles. The coating liquid C had a viscosity of 2.56 mPa·s.

The refractive index of a functional film was evaluated as follows. First, a functional film was formed on a polished surface side on a glass substrate (synthetic quartz having a diameter φ of 30 mm and a thickness of 1 mm and having one polished surface). The measurement was then performed in a wavelength region from 380 nm to 800 nm with a spectroscopic ellipsometer (VASE, manufactured by J. A. Woollam Japan). A refractive index at a wavelength of 550 nm was defined as the refractive index. The functional film used in this Example was confirmed to have a refractive index of 1.22. Formation of functional film on substrate Functional films were formed on a substrate as follows. The substrate used was a roll-shaped polyester film (LUMIRROR #188-U34, manufactured by Toray Industries, Inc., surface treatment <inner surface> adhesion-improving coating, surface treatment <outer surface> adhesion-improving coating) having a width of 300 mm and a length of 200 m. The films were formed by using a roll-to-roll coater (UVS-700, manufactured by LABO Co., Ltd.) as a film-forming apparatus. The coating method employed was a micro-gravure coating method, and a film formation speed was 2.5 m/min.

First, the coating liquid C was prepared in an apparatus pan. A ratio of the film formation speed to a rotational speed of a micro-gravure roll was adjusted such that the film thickness became 110 nm, and a functional film was then formed. Subsequently, a functional film was formed on the opposite surface under the same conditions. The drying temperature after the film formation was 80° C. The obtained light-transmitting member was cut and processed to have the shape illustrated in FIG. 4A.

The light-transmitting member was evaluated as follows. Evaluation of Transmittance of Light-Transmitting Member As a numerical value representing transparency of the light-transmitting member, a total luminous transmittance was evaluated in accordance with old JIS-K-7105 and JIS-K-7361 (spectrophotometer U-4000: manufactured by Hitachi High-Tech Corporation).

Evaluation of Haze of Light-Transmitting Member

As an index relating to transparency of the light-transmitting member, a haze was evaluated in accordance with old JIS-K-7105 and JIS-K-7136 (the same as the above).

Evaluation of Reflectivity of Light-Transmitting Member

As an index relating to transparency of the light-transmitting member, a reflectivity was evaluated. In order to prevent the measurement from being affected by reflection at the back surface, the back surface of the light-transmitting member to be measured was roughened with sandpaper (#800) in advance and then shielded from light with a black paint. The light-transmitting member prepared as described above was evaluated (reflectometer USPM-RU: manufactured by Olympus Corporation).

Evaluation of Visibility of Light-Transmitting Member

The light-transmitting member was cut and processed to have the shape illustrated in FIG. 4A. A face shield was produced, and the actual visibility was then checked. The evaluation was performed from the viewpoints of the presence or absence of glare due to external light such as a fluorescent lamp as viewed from the outside (the side on which the face shield is not worn) and the level of transparency as viewed from the inside (the side on which the face shield is worn) compared with the substrate itself on which no functional film was formed. Visibility was evaluated in accordance with the following criteria.

A: Visibility is significantly improved compared with the substrate on which no functional film is formed.

B: Visibility is improved to a certain degree compared with the substrate on which no functional film is formed.

C: There is no significant difference in visibility from the substrate on which no functional film is formed.

Evaluation of Wiping of Light-Transmitting Member

Wiping of the light-transmitting member was evaluated as follows. A polyester wiper (AlphaWipe TX1009, manufactured by Texwipe) was impregnated with pure water or a neutral detergent. The evaluation was performed under three wiping conditions including wiping with a dry wiper. The polyester wiper was moved on the light-transmitting member back and forth 10 times at a load of 200 g/cm$^2$ under each of the conditions. Subsequently, whether defects were generated or not on the light-transmitting member was evaluated by visual observation. The wiping was evaluated in accordance with the following criteria.

A: A good state where neither a scratch nor peeling is observed

B: A state where scratches are slightly observed

C: A state where scratches are noticeable, and peeling is partially observed

D: A state where the film is peeled off

Evaluation of Fogging Due to Breath

Breath was blown on the functional film of the light-transmitting member, and the presence or absence of fogging of the light-transmitting member was evaluated by visual observation. Fogging was evaluated in accordance with the following criteria.

A: Fogging does not occur.

B: Fogging slightly occurs.

C: Fogging occurs.

Tables 1 and 2 show conditions for the light-transmitting member of Example 1 and the evaluation results of the light-transmitting member of Example 1, respectively.

Example 2

A light-transmitting member was produced by using the same coating liquid C and the same substrate as those used in Example 1. Before the formation of a functional film, corona discharge treatment (80 W-min/m$^2$) was performed. Subsequently, the ratio to the rotational speed of the micro-gravure roll was adjusted such that the film thickness became 110 nm, and a functional film was then formed. Subsequently, the corona discharge treatment was not performed on the opposite surface, and a functional film was formed under the same conditions as those in Example 1 except for the above. The drying temperature after the film formation was 80° C. Tables 1 and 2 show conditions for the light-transmitting member of Example 2 and the evaluation results of the light-transmitting member of Example 2, respectively.

Example 3

A light-transmitting member was produced by using the same coating liquid C and the same substrate as those used in Example 1. The ratio to the rotational speed of the micro-gravure roll was adjusted such that the film thickness became 110 nm, and a functional film was then formed. Subsequently, the ratio to the rotational speed of the micro-gravure roll was changed such that the film thickness became 130 nm, and a functional film was formed on the opposite surface. The drying temperature after the film formation was 80° C. Tables 1 and 2 show conditions for the light-transmitting member of Example 3 and the evaluation results of the light-transmitting member of Example 3, respectively.

Example 4

A light-transmitting member was produced by using the same coating liquid C and the same substrate as those used in Example 1. The ratio to the rotational speed of the micro-gravure roll was adjusted such that the film thickness became 110 nm, and a functional film was then formed. Subsequently, the ratio to the rotational speed of the micro-gravure roll was changed such that the film thickness became 150 nm, and a functional film was formed on the opposite surface. The drying temperature after the film formation was 80° C. Tables 1 and 2 show conditions for the light-transmitting member of Example 4 and the evaluation results of the light-transmitting member of Example 4, respectively.

Example 5

A light-transmitting member was produced by using the same coating liquid C as that used in Example 1. The substrate used was a roll-shaped polyester film (LUMIRROR #125-UH13, manufactured by Toray Industries, Inc., surface treatment <inner surface> high-refractive adhesion-improving coating, surface treatment <outer surface> low-interference adhesion-improving coating) having a width of 300 mm and a length of 200 m. Films were formed by using a roll-to-roll coater (UVS-700, manufactured by LABO Co., Ltd.) as a film-forming apparatus. The coating method employed was a micro-gravure coating method, and a film formation speed was 2.5 m/min.

First, the coating liquid C was prepared in an apparatus pan. A ratio of the film formation speed to a rotational speed of a micro-gravure roll was adjusted such that the film thickness became 110 nm, and a functional film was then formed. Subsequently, a functional film was formed on the opposite surface under the same conditions. The drying temperature after the film formation was 80° C. Tables 1 and 2 show conditions for the light-transmitting member of Example 5 and the evaluation results of the light-transmitting member of Example 5, respectively.

Example 6

A light-transmitting member was produced by using the same coating liquid C as that used in Example 1. The substrate used was an A4-size sheet-shaped polyester film (LUMIRROR #250-T60, manufactured by Toray Industries, Inc., surface treatment <inner surface> none, surface treatment <outer surface> none). The films were formed by using a desktop coater (Model TC-1, manufactured by Mitsui Electric Co., Ltd.) as a film-forming apparatus. The coating method employed was a bar coater method, and a film formation speed was 2.5 m/min. A functional film was formed on one surface so as to have a thickness of 150 nm and then dried in a drying oven at 80° C. for five minutes. Subsequently, a functional film was formed on the other surface on the opposite side under the same conditions. Tables 1 and 2 show conditions for the light-transmitting member of Example 6 and the evaluation results of the light-transmitting member of Example 6, respectively.

Example 7

A light-transmitting member was produced by using the same coating liquid C as that used in Example 1. Functional films were formed under the same conditions for the substrate and the film formation method as those in Example 6 except that UV ozone cleaning (irradiation time: 15 minutes, irradiation distance: 10 mm) was performed as pretreatment. Tables 1 and 2 show conditions for the light-transmitting member of Example 7 and the evaluation results of the light-transmitting member of Example 7, respectively.

Example 8

A light-transmitting member was produced by using the same coating liquid C as that used in Example 1. Functional films were formed under the same conditions for the substrate and the film formation method as those in Example 6 except that corona discharge treatment (80 W·min/m$^2$) was performed as pretreatment. Tables 1 and 2 show conditions for the light-transmitting member of Example 8 and the evaluation results of the light-transmitting member of Example 8, respectively.

Example 9

A light-transmitting member was produced by using the same coating liquid C as that used in Example 1. The substrate used was the same as that used in Example 5. The ratio to the rotational speed of the micro-gravure roll was adjusted such that the film thickness became 110 nm, and a functional film was then formed on only one surface of the substrate. The drying temperature after the film formation was 80° C. Each of the evaluations was performed. Tables 1 and 2 show conditions for the light-transmitting member of Example 9 and the evaluation results of the light-transmitting member of Example 9, respectively.

Comparative Example

A light-transmitting member for comparison was produced as described below.
Preparation of Coating Liquid for Forming Functional Film A coating liquid D for forming a functional film was prepared by blending components having the composition below.

The composition includes 14.3 g of an isopropyl alcohol dispersion liquid of hollow silicon oxide particles (THRULYA 1110, manufactured by JGC Catalysts and Chemicals Ltd., average particle size: about 50 nm, shell thickness: about 10 nm, solid content: 20.5% by mass), 2.0 g of pentaerythritol triacrylate, 0.2 g of Irgacure 907 (manufactured by Ciba Specialty Chemicals Inc.), 0.2 g of TSF4460 (trade name, manufactured by GE Toshiba Silicones Co., Ltd. (currently Momentive Performance Materials Japan LLC), alkyl polyether-modified silicone oil), and 83.3 g of methyl isobutyl ketone. The prepared coating liquid D had a viscosity of 2.61 mPa·s.

The refractive index of a functional film was evaluated as follows. First, a functional film was formed on a polished surface side on a glass substrate (synthetic quartz having a diameter φ of 30 mm and a thickness of 1 mm and having one polished surface). The measurement was then performed in a wavelength region from 380 nm to 800 nm with a spectroscopic ellipsometer (VASE, manufactured by J. A. Woollam Japan). A refractive index at a wavelength of 550 nm was defined as the refractive index. The functional film used in Comparative Example had a refractive index of 1.27.
Formation of Functional Film on Substrate A porous film was formed by using the prepared coating liquid D. The substrate used was an A4-size sheet-shaped polyester film (LUMIRROR #250-T60, manufactured by Toray Industries, Inc., surface treatment <inner surface> none, surface treatment <outer surface> none). The film was formed by using a desktop coater (Model TC-1, manufactured by Mitsui Electric Co., Ltd.) as a film-forming apparatus. The coating method employed was a bar coater method, and a film formation speed was 2.5 m/min. The functional film was formed on only one surface of the substrate so as to have a thickness of 2,000 nm. After the film formation, the functional film was dried at a drying temperature of 80° C. for five minutes. The obtained light-transmitting member was cut and processed to have the shape illustrated in FIG. 4A, and each of the evaluations was performed. Tables 1 and 2 show conditions for the light-transmitting member of Comparative Example and the evaluation results of the light-transmitting member of Comparative Example, respectively.

TABLE 1

| | | | | Light-transmitting member | | | | |
| | | | | Substrate | | | Functional film | |
| | Coating liquid | Film formation method | Material | Thickness (μm) | Adhesion-improving layer | Coating pretreatment | Forming surface | Physical thickness (nm) |
|---|---|---|---|---|---|---|---|---|
| Example 1 | Coating liquid C | Micro-gravure | PET | 188 | Present | — | Both surfaces | 110/110 |

TABLE 1-continued

| | | | Light-transmitting member | | | | | |
| | | | Substrate | | | | Functional film | |
| | Coating liquid | Film formation method | Material | Thickness (μm) | Adhesion-improving layer | Coating pretreatment | Forming surface | Physical thickness (nm) |
|---|---|---|---|---|---|---|---|---|
| Example 2 | Coating liquid C | Micro-gravure | PET | 188 | Present | Corona treatment (one surface) | Both surfaces | 110/110 |
| Example 3 | Coating liquid C | Micro-gravure | PET | 188 | Present | — | Both surfaces | 110/130 |
| Example 4 | Coating liquid C | Micro-gravure | PET | 188 | Present | — | Both surfaces | 110/150 |
| Example 5 | Coating liquid C | Micro-gravure | PET | 125 | Present | — | Both surfaces | 110/110 |
| Example 6 | Coating liquid C | Bar coater | PET | 250 | Absent | — | Both surfaces | 150/150 |
| Example 7 | Coating liquid C | Bar coater | PET | 250 | Absent | $UV/O_3$ | Both surfaces | 150/150 |
| Example 8 | Coating liquid C | Bar coater | PET | 250 | Absent | Corona treatment | Both surfaces | 150/150 |
| Example 9 | Coating liquid C | Micro-gravure | PET | 125 | Present | — | One surface | 110 |
| Comparative Example | Coating liquid D | Bar coater | PET | 250 | Absent | — | One surface | 2000 |

TABLE 2

| | Evaluation results of light-transmitting member | | | | | | |
| | | | | Evaluation of wiping | | | |
| | Transmittance (%) | Haze (%) | Evaluation of visibility | Dry wiper | Pure water | Neutral detergent | Evaluation of fogging |
|---|---|---|---|---|---|---|---|
| Example 1 | 99.8 | 0.3 | A | B | B | A | A |
| Example 2 | 99.7 | 0.3 | A | B | B | A | A |
| Example 3 | 99.5 | 0.3 | A | B | B | A | A |
| Example 4 | 99.1 | 0.4 | A | A | B | B | A |
| Example 5 | 98.8 | 0.5 | A | B | A | A | A |
| Example 6 | 96.9 | 2.2 | A | C | C | D | A |
| Example 7 | 97.2 | 2.2 | A | A | A | B | A |
| Example 8 | 96.4 | 2.3 | B | B | A | B | A |
| Example 9 | 92.7 | 0.9 | B | B | B | B | A |
| Comparative Example | 88.3 | 0.4 | C | A | A | B | B |

The results in Table 2 demonstrated that Examples could realize good functionality as a face shield.

The embodiments described above can be appropriately changed without departing from the technical idea. The embodiments can provide a technology advantageous to improvement in the functionality of a light-transmitting member. The disclosure of the present specification encompasses, in addition to the descriptions of this specification, all the matters that can be understood from the present specification and the drawings attached to the present specification.

With regard to specific ranges of numerical values described as examples, the expression of e to f (where e and f are numerals) means e or more and/or f or less. With regard to specific ranges of numerical values described as examples, when both a range of i to j and a range of m to n are described (where i, j, m, and n are numerals), the pair of the lower limit and the upper limit is not limited to a pair of i and j or a pair of m and n. For example, combinations of a lower limit and an upper limit of a plurality of pairs may also be considered. Specifically, when both a range of i to j and a range of m to n are described, consideration may be made in a range of i to n, or consideration may be made in a range of m to j.

The disclosure of the present specification encompasses the complementary sets of the individual concepts described in the present specification. Specifically, for example, if the present specification includes a description "A is greater than B", the present specification is regarded as disclosing "A is not greater than B" even if the description "A is not greater than B" is omitted. This is because the description "A is greater than B" is based on the assumption that the case of "A is not greater than B" is considered.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-171319 filed Oct. 9, 2020, which is hereby incorporated by reference herein in its entirety.

What is claimed is:

1. A light-transmitting member having a first surface and a second surface, comprising:
    a substrate having a first main surface and a second main surface opposed to each other, and including one resin layer at least; and
    a first functional film disposed on the first main surface of the substrate, the first functional film forming the first surface,
    a second functional film disposed on the second main surface of the substrate, the second functional film forming the second surface,
    wherein a distance between the first functional film and the second functional film is 1 μm or more and less than 1 mm,
    an optical thickness of the first and second functional films with respect to light having a wavelength of 464 nm or more and 653 nm or less is less than a half of the wavelength,
    a contact angle of water with respect to the first and second surfaces of the light-transmitting member is less than 90°,
    the first and second functional films have a porous portion containing a plurality of particles, a first particle and a second particle among the plurality of particles are bound to each other with a binder,
    each of the first particle and the second particle contains silica, and the binder contains a silicate,
    a distance between the one resin layer and the first functional film is less than a physical thickness of the first functional film, and
    a distance between the one resin layer and the second functional film is less than a physical thickness of the second functional film.

2. The light-transmitting member according to claim 1, wherein the binder does not contain a resin.

3. The light-transmitting member according to claim 1, wherein the wavelength is 509 nm or more and 614 nm or less.

4. The light-transmitting member according to claim 1, wherein the first functional film has a refractive index of less than 1.30.

5. The light-transmitting member according to claim 1, wherein the one resin layer is formed of a crystalline resin.

6. The light-transmitting member according to claim 1, wherein a thickness of the substrate is 100 μm or more and less than 250 μm.

7. The light-transmitting member according to claim 1, wherein a distance between the one resin layer and the porous portion of the first functional film is smaller than a physical thickness of the porous portion of the first functional film, and a distance between the one resin layer and the porous portion of the second functional film is smaller than a physical thickness of the porous portion of the second functional film.

8. A package unit comprising:
    at least three light-transmitting members that overlap one another; and
    a package that contains the three light-transmitting members,
    wherein each of the three light-transmitting members is the light-transmitting member according to claim 1.

9. A wound body comprising:
    the light-transmitting member according to claim 1; and
    a core,
    wherein the light-transmitting member is wound around the core.

10. A shield comprising:
    The light-transmitting member according to claim 1; and
    a holder that holds the light-transmitting member.

11. The shield according to claim 10, wherein the holder has a structure configured to fix the light-transmitting member to a user such that the light-transmitting member covers at least part of a face of the user.

12. The shield according to claim 10, wherein a surface of the light-transmitting member is a curved surface.

13. The shield according to claim 10, comprising:
    a ventilation fan configured to ventilate an atmosphere adjacent to the light-transmitting member.

14. An apparatus comprising:
    the light-transmitting member according to claim 1; and
    a light-transmitting component covered with the light-transmitting member.

15. A light-transmitting member having a first surface and a second surface, comprising:
    a substrate having a first main surface and a second main surface opposed to each other, and including one resin layer at least; and
    a first functional film disposed on the first main surface of the substrate, the first functional film forming the first surface,
    a second functional film disposed on the second main surface of the substrate, the second functional film forming the second surface,
    wherein a distance between the first functional film and the second functional film is 1 μm or more and less than 1 mm,
    an optical thickness of the first and second functional films with respect to light having a wavelength of 464 nm or more and 653 nm or less is less than a half of the wavelength,
    the first and second surfaces of the light-transmitting member provide hydrophilicity or hydrophobicity,
    the first and second functional films have a porous portion containing a plurality of particles, a first particle and a second particle among the plurality of particles are bound to each other with a binder that does not contain a resin, a distance between the first particle and a third particle among the plurality of particles is smaller than a size of the first particle, an empty space is provided between the first particle and the third particle, and
    each of the first particle, the second particle, the third particle, and the binder contains a material containing silicon and oxygen,
    a distance between the substrate and the porous portion of the first functional film is less than a physical thickness of the first functional film, and
    a distance between the substrate and the porous portion of the second functional film is less than a physical thickness of the second functional film.

16. The light-transmitting member according to claim 15, wherein each of the first particle and the second particle is a hollow particle or a chain-like particle.

17. The light-transmitting member according to claim 16, wherein the first functional film includes a protective layer covering the plurality of particles in the first functional film.

18. The light-transmitting member according to claim 15, having a maximum width of 2 cm or more and 2 m or less.

19. The light-transmitting member according to claim 15, having at least one of a notch and a hole.

20. A method for manufacturing the light-transmitting member according to claim 15, the method comprising:
    providing a wound body formed of the substrate that is wound;

spreading the substrate of the wound body;
forming the first and second functional films on the spread substrate by a wet film-forming method; and
winding the substrate on which the first and second functional films are formed.

21. A method for manufacturing an article, comprising:
observing a product and/or a manufacturing apparatus through the light-transmitting member according to claim 15.

22. A light-transmitting member having a first surface and a second surface, comprising:
a substrate having a first main surface and a second main surface opposed to each other, and including one resin layer at least; and
a first functional film disposed on the first main surface of the substrate, the first functional film forming the first surface,
a second functional film disposed on the second main surface of the substrate, the second functional film forming the second surface,
wherein a distance between the first functional film and the second functional film is 1 μm or more and less than 1 mm,
the first and second functional films have a physical thickness smaller than a thickness of the substrate,
a contact angle of water with respect to the first and second surfaces of the light-transmitting member is less than 90°,
the first and second functional films have a porous portion containing a plurality of particles, a distance between a first particle and a second particle among the plurality of particles is smaller than a size of the first particle, an empty space formed by the first particle and the second particle is provided between the first particle and the second particle,
each of the first particle and the second particle is a hollow particle,
a distance between the one resin layer and the porous portion of the first functional film is smaller than a physical thickness of the porous portion of the first functional film, and
a distance between the one resin layer and the porous portion of the second functional film is smaller than a physical thickness of the porous portion of the second functional film.

23. The light-transmitting member according to claim 22, wherein the substrate has a thickness of 100 μm or more and less than 1 mm, and the first and second functional films have a physical thickness of less than 200 nm.

24. The light-transmitting member according to claim 22, wherein each of the first particle and the second particle is smaller than SARS-COV-2.

25. The light-transmitting member according to claim 22, wherein the first and second functional films have a physical thickness larger than a sum of the size of the first particle and a size of the second particle.

26. The light-transmitting member according to claim 22, wherein the contact angle of water with respect to the first and second surfaces of the light-transmitting member is 45° or less.

27. The light-transmitting member according to claim 22, having an average transmittance of 95.0% or more in a wavelength region of 400 nm or more and 700 nm or less.

28. The light-transmitting member according to claim 22, wherein the one resin layer is formed of a polyester resin.

29. The light-transmitting member according to claim 22, wherein an outer periphery of the light-transmitting member includes a curved portion having a radius of curvature of 1 mm or more.

30. A method for producing a picture, comprising:
capturing an image of an object through the light-transmitting member according to claim 22 to produce a picture.

31. A shield comprising:
the light-transmitting member according to claim 22; and
a holder that holds the light-transmitting member,
wherein the holder has a structure configured to fix the light-transmitting member to a user such that the light-transmitting member covers at least a mouth of the user,
a portion of the light-transmitting member that covers at least the month includes the substrate, the first functional film and the second functional film.

32. The shield according to claim 31, wherein the plurality of particles of the porous portion of the second functional film are bound together with a material having a siloxane bond.

33. The shield according to claim 31, wherein the contact angle of water with respect to the first and second surfaces of the light-transmitting member is 45° or less.

34. The shield according to claim 31, wherein a thickness of the substrate is 100 μm or more and less than 1 mm, and the physical thickness of the first and second functional films is less than 200 nm.

35. The shield according to claim 31, wherein a distance between a third particle and a fourth particle among the plurality of particles in the porous portion of the second functional film is smaller than a size of the third particle, and an empty space formed by the third particle and the fourth particle is provided between the third particle and the fourth particle.

36. The shield according to claim 31, wherein the plurality of particles in the porous portion of the second functional film include a hollow particle.

* * * * *